United States Patent [19]
Toh

[11] Patent Number: 6,046,803
[45] Date of Patent: Apr. 4, 2000

[54] TWO AND A HALF DIMENSION INSPECTION SYSTEM

[75] Inventor: Peng Seng Toh, Parc Oasis, Singapore

[73] Assignee: Hewlett-Packard Company, Palo Alto, Calif.

[21] Appl. No.: 08/995,111

[22] Filed: Dec. 19, 1997

[30] Foreign Application Priority Data

May 20, 1997 [SG] Singapore ............................ 9701603-4

[51] Int. Cl.[7] .................................................. G01N 21/88
[52] U.S. Cl. .................................................... 356/237.2
[58] Field of Search .............................. 356/394, 237.2, 356/237.3, 237.4

[56] References Cited

U.S. PATENT DOCUMENTS

| | | | |
|---|---|---|---|
| 4,242,702 | 12/1980 | Kuni et al. | 356/394 |
| 4,449,818 | 5/1984 | Yamaguchi et al. | 356/237.3 |
| 4,581,706 | 4/1986 | Kato et al. | 356/394 |
| 4,692,690 | 9/1987 | Hara et al. | 356/394 |
| 5,331,397 | 7/1994 | Yamanaka et al. | 356/394 |
| 5,369,492 | 11/1994 | Sugawara | 356/394 |
| 5,519,496 | 5/1996 | Borgert et al. | 356/394 |

*Primary Examiner*—Richard A. Rosenberger

[57] ABSTRACT

An inspection system for detecting surface defects on an object is disclosed, which includes a light source operable to emit a broad spectrum visible light to illuminate the object and a video source operable to receive an image from light reflected from the object surface at a predetermined direction. The system further includes an image processor operable to compare the intensity of the reflected light received by the video source with a range of predetermined intensity values so as to detect defects on the object surface. The inspection system is particularly suited for use in semiconductor manufacturing.

1 Claim, 6 Drawing Sheets

TWO AND A HALF DIMENSION INSPECTION SYSTEM

FIELD OF THE INVENTION

The present invention relates to an inspection system for detecting defects in the surface of an object. The invention is related more particularly to detecting defects on the surface of integrated circuits.

BACKGROUND

In semiconductor manufacturing, the inspection for defects on integrated circuit (IC) package and leads are common. Some of the defects require true three dimensional (3D) inspection. However, space constraints often limits the use of true 3D imaging that typically involves multiple cameras. Such constraints are particularly severe, in semiconductor packaging operation where an IC can only be viewed from a limited direction, such as the top. Thus space constraints precludes the use of multiple cameras viewing the IC from different directions. Fortunately, some of the defects can be determined by using implied 3D from 2D rather than true 3D imaging. Usually such defects are the type that do not need to be quantitatively determined. A qualitative approach is usually sufficient and hence true 3D imaging is not necessary.

Previous inspection systems employing 3D imaging techniques include the use of laser scanning to detect bent lead (downward or upward), pit, dent and other similar defects. A laser scanning method that involves the use of a laser to scan the surface of the object and detect the dispersion of the laser beam has also been used. Another approach of the laser scanning method is to detect the height (Z dimension) of the object through the use of laser triangulation. The three dimensional profile of the object surface can be determined and compared with a known good sample. Whilst these systems are effective, they suffer from the disadvantages of being expensive to implement and relatively slow due to the time required for the laser to scan the surface to complete the inspection.

SUMMARY OF INVENTION

In one aspect, present invention provides an inspection system that uses 2D imaging but is easier to implement and quicker than previous laser scanning techniques.

In one embodiment of an inspection system for detecting surface defects on an object according to the present invention, the system includes:

a light source operable to illuminate the object;

a sensor operable to receive light reflected in a predetermined direction from the object surface; and a processor operable to detect the defects on the object surface by comparing the intensity of the reflected light received by the sensor with a predetermined range of intensity values.

One advantage of the present invention is that the system uses the intensity of light to differentiate between a good surface and that of a defective surface. By making an assessment based on the intensity of light the response time of the system is faster than previous laser scanning techniques and such an apparatus of the present invention for carrying out the inspection is less expensive than prior apparatuses.

Preferably the light from said light source is diffuse (therefore noncoherent) and is emitted in a first direction to impinge on the surface of the object. In a preferred form, the predetermined direction of reflected light is substantially parallel to this first direction.

Preferably the light emitted from the light source is visible light over a broad spectrum.

The present invention is especially well suited to apply when the surface of the object to be inspected is substantially planar and is located perpendicular to the first direction.

Preferably the sensor is in the form of a video source and incorporates an optical axis which is parallel to the direction of the light rays emitted from the light source. In this way, the video source can receive light reflected from the object surface at a direction parallel to the direction of the light rays emitted from the light source.

Preferably, the processor is in the form of an image processor. Preferably the inspection system is arranged such that the image processor is able to establish the predetermined range of intensity values by the inspection of at least one control object. In this way, different ranges of intensity values can be established for different surface areas and under different conditions. An advantage of using the inspection of a control to establish the range is that it minimises errors that may otherwise occur through variations in operational conditions.

In a further aspect, the present invention provides a method of detecting defects on the surface of an object. An embodiment of the method includes the steps of:

illuminating the surface of an object with a light source;

measuring the intensity of light reflected in a predetermined direction from the surface; and detecting defects on the surface based on a comparison of the intensity of the reflected light with a predetermined range of intensity values.

Preferably light rays from the light source are emitted in a first direction to impinge on the surface of the object, and that the predetermined direction of the reflected light is substantially parallel to this first direction.

The inspection system of the present invention is well suited to inspecting objects with generally flat areas and is particularly well suited for inspecting semiconductors such as the moulded package body and leads of a semiconductor device. In use, for example, in a preferred form, an on axis diffused light is used to illuminate a semiconductor device such as an integrated circuit. The light source is sufficiently diffused and the light emitting direction is parallel to the optical axis of a viewing video source such as a video camera. The surface of the integrated circuit is placed perpendicular to the optical axis of the video source. The light ray emitting from the light source along the direction of the optical axis is reflected back from the object to the video source. In the case where the object surface is flat without defects such as bent upward/downwards, pits, voids, dents, the reflected light will travel along the optical axis and return to the video source. In the case where there are defects in the third dimension, the reflected light will be diverted and the amount of reflected light along the optical axis will be reduced.

According to a preferred form, the processor, which is typically an image processor, is used to differentiate between a good surface with that of a defective surface. The image processor analyses the video source intensity values of the area of interest to check for defect. This analysis is made by a comparison of the intensity of the reflected light with the intensity of a predetermined range of intensity values stored in the processing device.

DESCRIPTION OF ACCOMPANYING DRAWINGS

SPECIFIC EMBODIMENT

Figure 1:
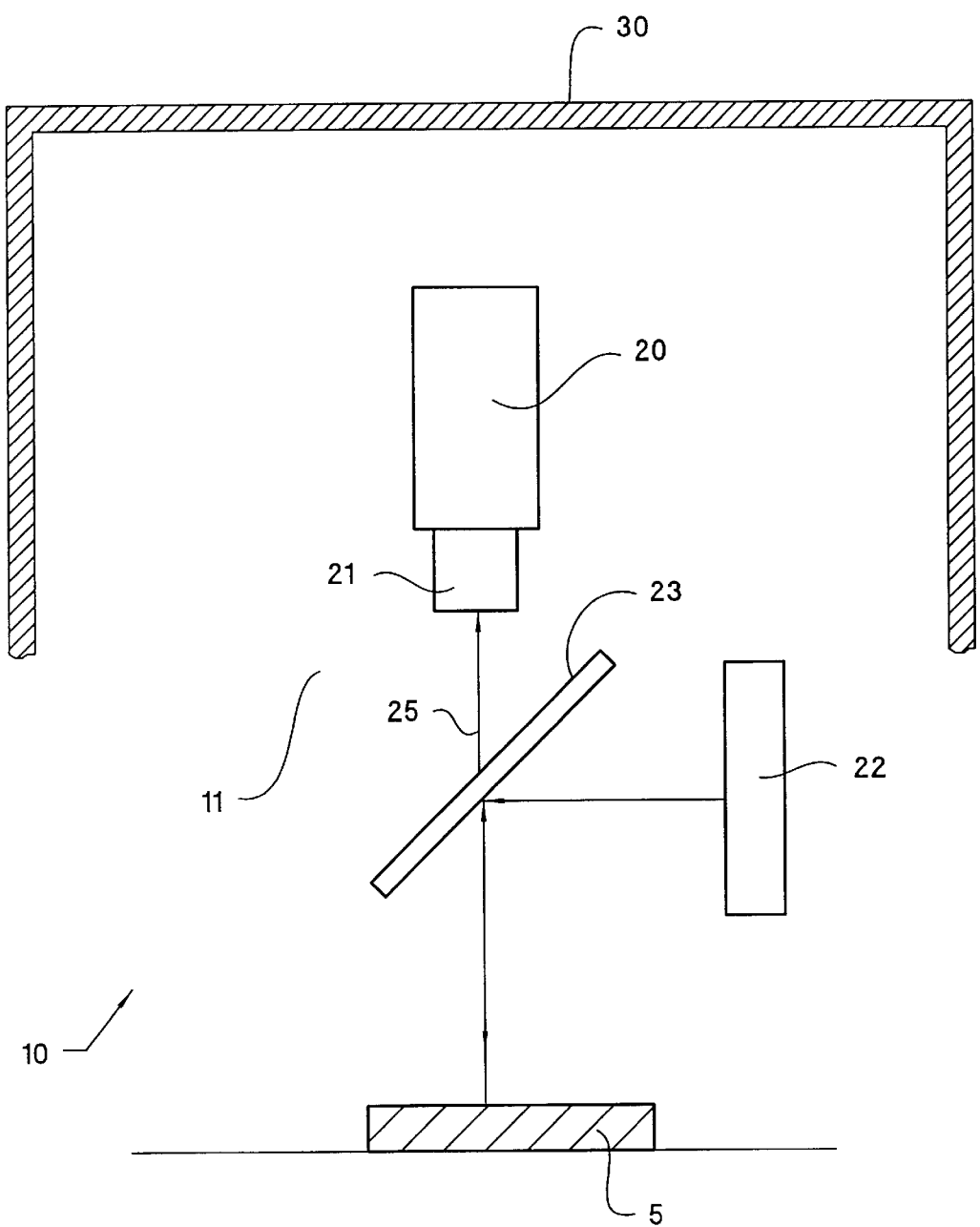
FIG. 1 is a schematic view of the optical module of an inspection system according to an embodiment of the present invention.

FIG. 1 illustrates an optical module 11 which forms part of an inspection system 10 for detecting surface defects on an object. The module 11 includes a video source, typically a video camera 20 with an appropriate lens 21, and an area light source 22 that is properly diffused and has a broad spectrum. A beam splitter 23 is positioned between the video camera 20 and the light source 22 such that the direction of the illuminating light ray is parallel to the optical axis 25 of the system. Using the accompanied drawing of FIG. 1 as an example, the light source 22 emits light that transmits through the beam splitter to reach the object 5. The surface of the object 5 is planar and arranged perpendicular to the optical axis. In this way, if the surface is without defects, the light reflected from the object 5 will travel in parallel to the optical axis 25 and be reflected from the beam splitter 23 to reach the video camera 20 through the lens 21. An enclosure 30 is provided to shield the lighting and viewing system from ambient and stray lights.

Figure 2:
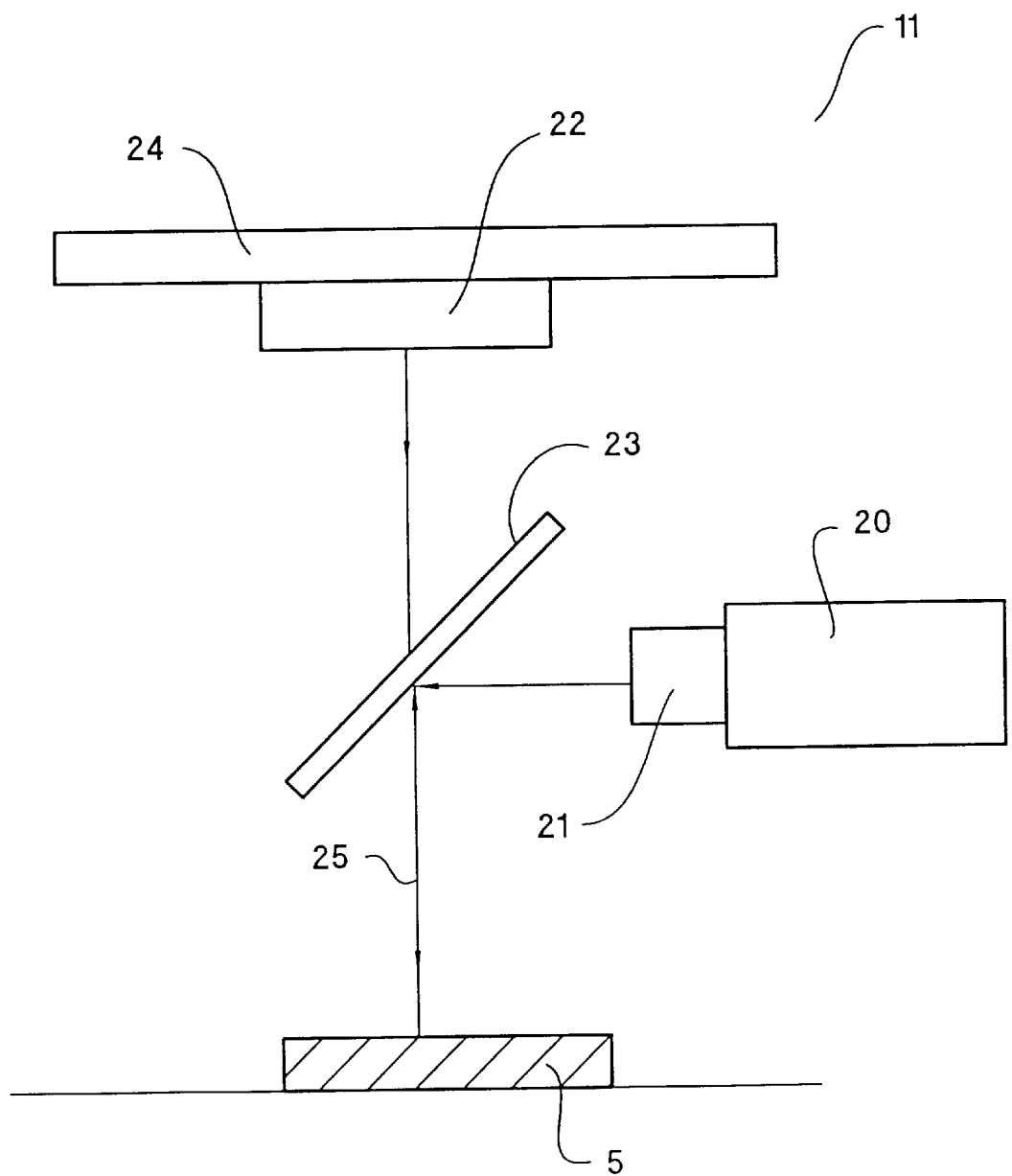
FIG. 2 is a variation of the optical module of FIG. 1.

FIG. 2 of the accompanied drawings illustrates an alternative to FIG. 1. In this arrangement, light emitting from the light source 22 gets reflected from the beam splitter 23 to illuminate the object 5. Again, if the object surface is not defective, reflected light from the object travels in parallel to the optical axis 25 and passes through the beam splitter 23 to reach the video camera 20. A light absorbing material 24 is placed at the opposite side of the light source to absorb unwanted lights that passes through the beam splitter 23. Furthermore, in order to prevent a ghostly image from happening, the beam splitter 23 is coated with anti-reflection coating on its non-reflecting surface.

The light source 22 has a broad spectrum spanning the entire visible range from blue to red. This enables all types of surface with different colours or tones to be imaged. In the case of using a narrow spectrum light source such as LED, if the colour of the object does not match that of the LED light source, then the reflected light will be very weak. Using a narrow spectrum light source will not be able to tolerate variations in the object colour. In other words, if there is a slight variation in the colour of the object, then the system using narrow spectrum light source will not function properly. On the other hand, the use of wide spectrum light source will allow the slight variation in colour to appear on the same object as well as between objects. In practice, such variation often exists when the object is an integrated circuit.

Figure 5:
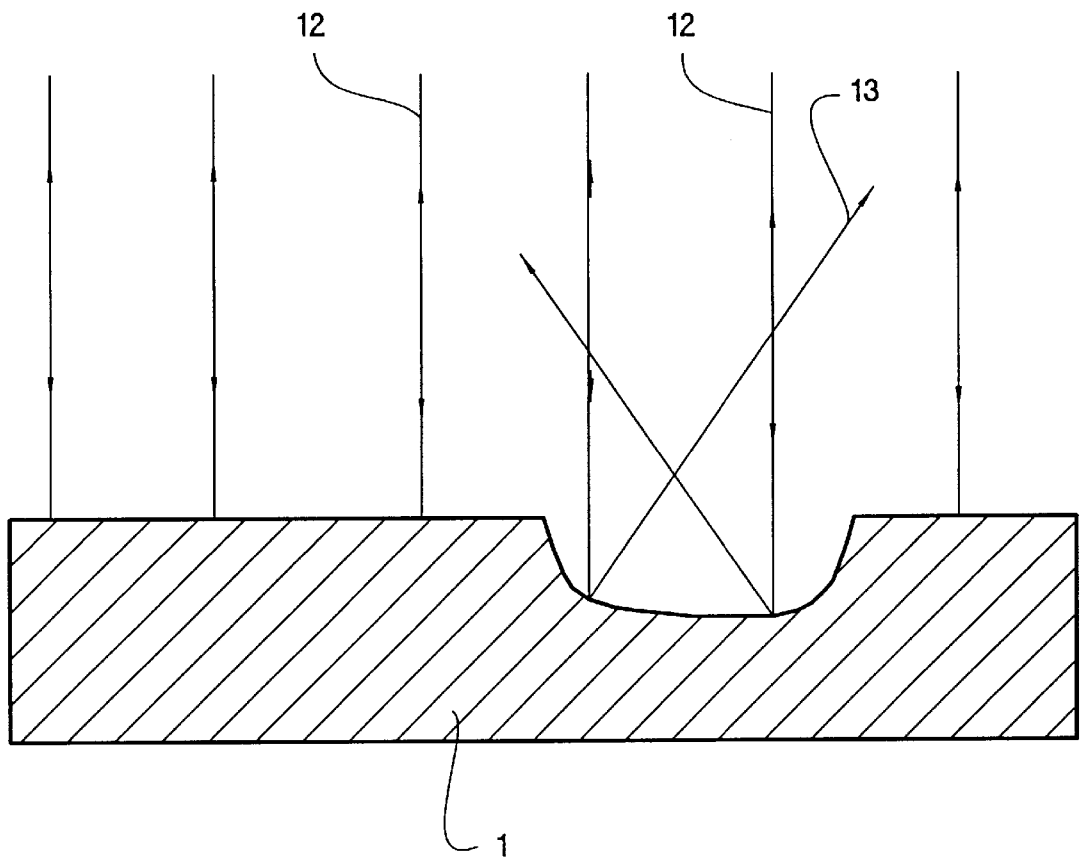
FIG. 5 is a detailed view of a plastic package of the integrated circuit of FIG. 4.
Figure 6A:
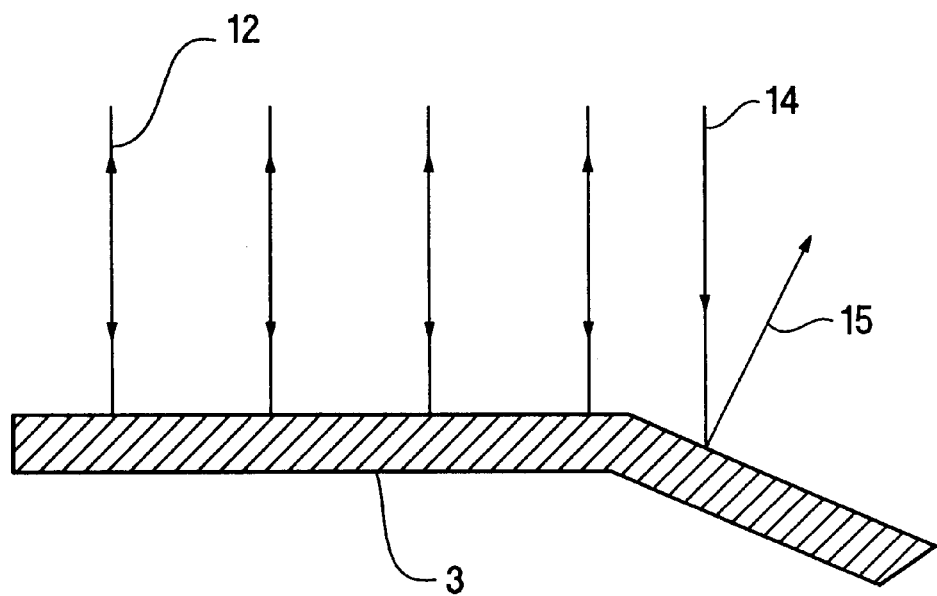
FIGS. 6A and 6B are detailed views of portions of a lead of the integrated circuit of FIG. 4.
Figure 6B:
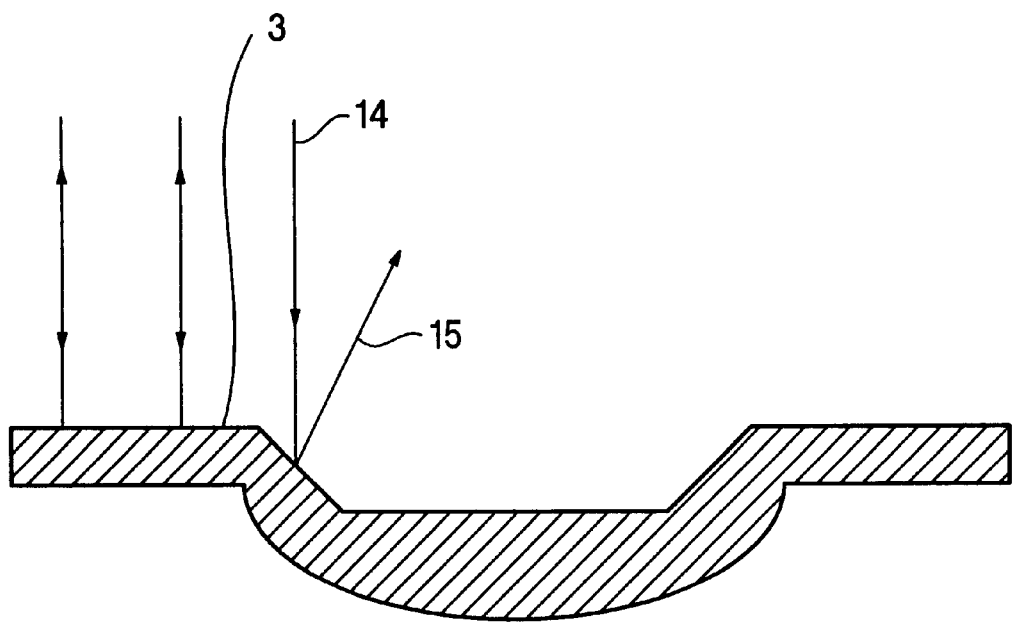

As illustrated in FIG. 5 and FIG. 6 an object 5 with even surface, the reflected light 12 will travel along the direction where it comes from. However, in the case where there is a change in surface orientation, then the reflected light 15 will not be reflected in the illuminating direction 14. In this case, the video camera 20 will not receive the same amount of light as that of an even surface.

In the case where the object is an IC, such a defect can occur to the leads of an IC which is bent downward or upward (see FIG. 6). Similarly, a defect such as a pit can occur on the plastic package 1 of an IC (see FIG. 5). The pit causes the reflected light 13 to be directed away from the optical axis 25, hence it does not fully reflect back to the video camera 20.

Figure 3:
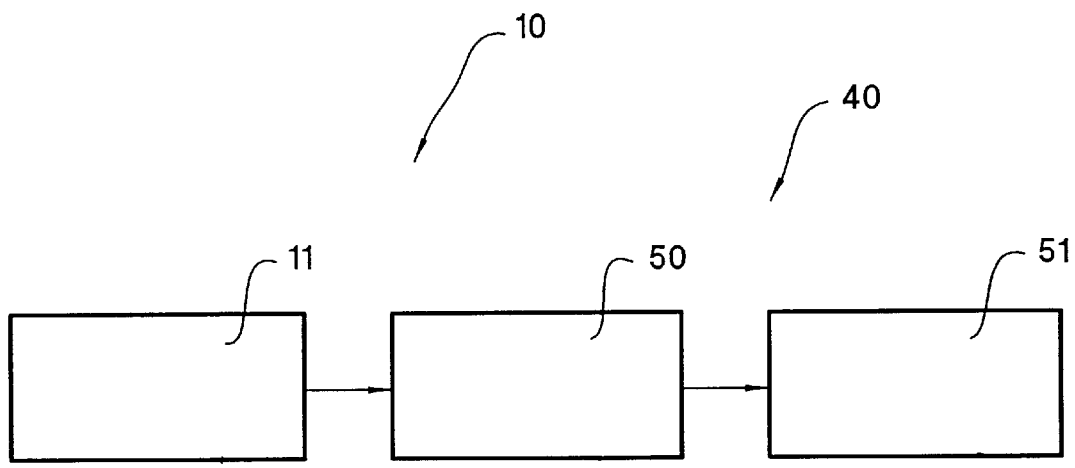
FIG. 3 is a block diagram of the inspection system according to an embodiment of the present invention.

The inspection system 10 includes an image processor 40 (see FIG. 3) that analyses the image received by the video source so as to detect whether the object surface is defective. As illustrated in FIG. 3, the video camera 20 sends the image of the object to the frame grabber 50 such that the video information is converted to digital format and can be processed by the processor 51. The processor 51 is typically a computer such as a personal computer or a dedicated image processing system. The processor 51 uses an algorithm to process the image and make a determination whether the surface is defective.

The image processor 40 can analyse inspection information in two stages: teach and inspect. In an embodiment the image processor works on the gray scale image that has an intensity range of 2k, where k is normally 8. The teach phase establishes parameters relating to areas within the image that needs to be inspected (known as the area of interest). The parameters that will be learned by the processor 51 is the average intensity value and the intensity variance of the area of interest. The teach phase is carried out using physical samples placed in the optical module 11, which establishes the limits of these parameters such that a predetermined range of intensity values is established for the area of interest. This predetermined range is the criteria (i.e., a model) upon which the processor determines whether the area of interest is defective or not. If the reflected light from the inspected object falls within this predetermined range, the object is acceptable. If it is outside this range, the system regards the object as defective.

Upon the completion of the teach phase, the criteria (or model) can be used for implementing the inspection of the object. The object to be inspected is placed under the optical module of the system 10 and the image of the object 5 is captured by the video camera 20. The area of interest within the image is analysed by the image processor to determine whether the average intensity and the variance is within the allowable limits of the pre-stored taught values.

Figure 4A:
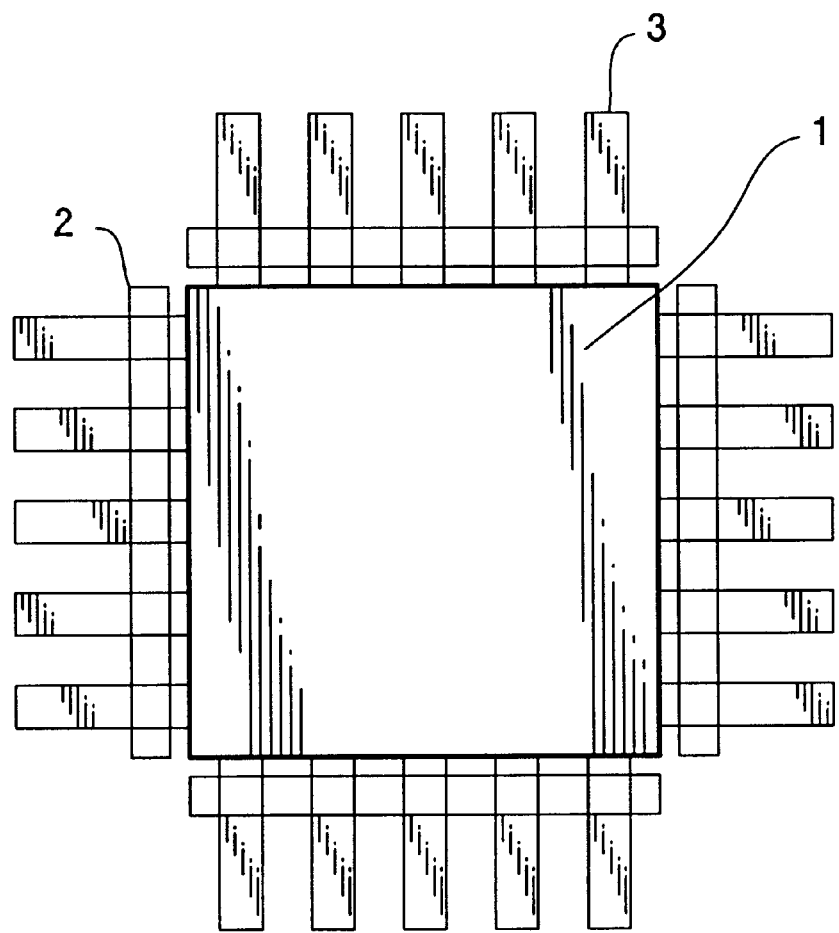
FIGS. 4A and 4B are a schematic plan view and schematic side view of an integrated circuit (IC) package.
Figure 4B:
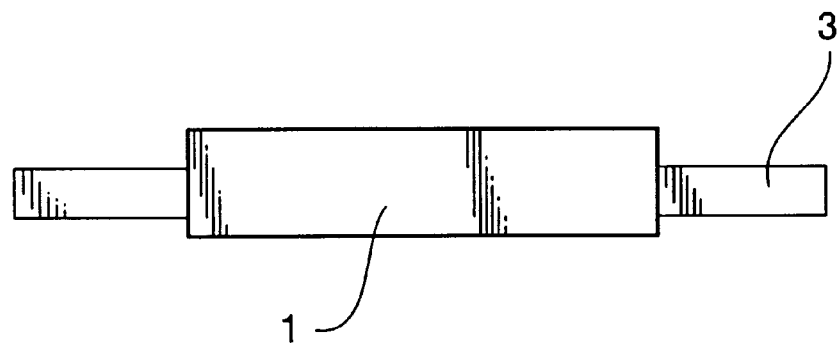

A typical application of the inspection system 10 is to check the mould defects and the dam bar cutting defects associated with the semiconductor assembly process. FIGS. 4 to 6 to show examples of defects in IC packages. As illustrated in FIGS. 4 to 6, the mould defect is associated with the plastic package 1 of an IC and the dam bar cutting defect is associated with the leads 3 of the IC. The dam bar 2 is usually located at the edges of the IC package 1. The mould defects generally include pit, incomplete fill, and exposure metal among others. The dam bar cut defects include partial broken leads, burr, uncut and completely broken leads. The system 10 is particularly effective in detecting partially broken lead defects involving a change in surface orientation. The system can be applied to inspect immediately after the dam bar cutting process before the forming of the leads takes place. On a good IC, the mould package 1 is generally flat, as are the leads. In order to inspect for defective leads, the image of the IC can be acquired and the image processor can be used to analyse the average intensity of the leads and their intensity variation. For example, the image processor will learn that on good leads 3, the average intensity is $I_n$ with a maximum deviation of $dI$. The deviation in the average intensity is mainly due to the slight variation in colour. The average intensity of a defective lead (such as bent lead) will be lower than $(I_n-dI)$. Hence, by analysing the average intensity of all the leads 32, defective leads can be detected.

It will be understood that various alterations and/or modification may be made to the embodiments described herein without departing from the spirit or ambit of the present invention.

What is claimed is:

1. A method of detecting defective leads in a leaded integrated circuit package, comprising:

illuminating the leads of the integrated circuit package using a light source, sensing light reflected in a predetermined direction from the leads of the integrated circuit package and generating for each lead of the integrated circuit package a signal corresponding to the intensity of light reflected from that lead, processing the signals for all the leads to determine the average intensity of light reflected from the leads ($I_n$) and the variation of the intensity of light (dI) reflected from the leads, and comparing the signal corresponding to the intensity of light reflected for each lead with the average intensity of light and the variation of the intensity of light to determine if each lead is defective.

* * * * *